(12) United States Patent
Boels et al.

(10) Patent No.: US 10,683,529 B2
(45) Date of Patent: Jun. 16, 2020

(54) KIT FOR DETECTING BIOFILMS

(71) Applicant: REALCO, Louvain-la-Neuve (BE)

(72) Inventors: Gauthier Boels, Brussels (BE);
Gordon Blackman, Lasnes (BE);
Almudena Calabozo,
Louvain-la-Newuve (BE)

(73) Assignee: REALCO, Louvain-La-Nueve (BE)

( * ) Notice: Subject to any disclaimer, the term of this patent is extended or adjusted under 35 U.S.C. 154(b) by 258 days.

(21) Appl. No.: 14/601,158

(22) Filed: Jan. 20, 2015

(65) Prior Publication Data

US 2015/0132796 A1    May 14, 2015

Related U.S. Application Data

(62) Division of application No. 14/126,320, filed as application No. PCT/EP2012/062086 on Jun. 22, 2012, now abandoned.

(30) Foreign Application Priority Data

Jun. 24, 2011   (EP) ..................................... 11171360

(51) Int. Cl.
```
C12Q 1/04     (2006.01)
C12Q 1/22     (2006.01)
G01N 33/52    (2006.01)
```

(52) U.S. Cl.
CPC ................. C12Q 1/04 (2013.01); C12Q 1/22 (2013.01); G01N 33/52 (2013.01)

(58) Field of Classification Search
CPC ............. C12Q 1/04; C12Q 1/22; G01N 33/52
See application file for complete search history.

(56) References Cited

U.S. PATENT DOCUMENTS

| | | | |
|---|---|---|---|
| 5,112,749 A | 9/2000 | Hall et al. | |
| 6,117,423 A | 9/2000 | Berg | |
| 2002/0085980 A1 | 7/2002 | Fuglsang | |
| 2003/0205247 A1 | 11/2003 | Lengling et al. | |
| 2010/0015245 A1 * | 1/2010 | Harrison | A01N 59/02 424/615 |

FOREIGN PATENT DOCUMENTS

| | | | |
|---|---|---|---|
| EP | 1491505 A1 * | 5/2004 | ................ C02F 1/00 |
| EP | 1491505 | 12/2004 | |
| EP | 1536225 | 6/2005 | |
| EP | 2243821 | 10/2010 | |
| FR | 2928457 | 9/2009 | |
| JP | 2005210997 | 8/2005 | |
| WO | WO-2001053010 A1 * | 7/2001 | ......... C11D 11/0011 |

OTHER PUBLICATIONS

Hervieu G. www.mundilab.com. 2001;1-2.*
Zufferey et al. Simple Method for Rapid Diagnosis of Catheter-Associated Infection by Direct Acridine Orange Staining of Catheter Tips. Journal of Clinical Microbiology. 1988;175-177.*
T.A. Trozzi et al., "Processing Guide for Developing Latent Prints," U.S. Department of Justice, Federal Bureau of Investigation, Laboratory Division, revised 2000, 70 pages.
NOIDA. Sodium perborate. NOIDA Chemicals. 2009; 1-5.
Lindsay. Natural stain remover & cleaning agent: hydrogen peroxide! Passionate Homemaking. 2009;1-2.
European Patent Office Search Report dated Jul. 20, 2012, International Patent Application No. PCT/EP2012/062086, Applicants: Boels et al. (6 pages).
Candiano et al. Blue silver: a very sensitive colloidal Coomassie G-250 staining for proteome analysis. Electrophoresis. 2004;25:1327-1333.
Marchant, B., and Tague, C., "Developing Fingerprints in Blood: A Comparison of Several Chemical Techniques," Journal of Forensic Identification 76/57(1), Jan. 2007, 18 pages.

* cited by examiner

*Primary Examiner* — Lynn Y Fan
(74) *Attorney, Agent, or Firm* — Chistensen O'Connor Johnson Kindess PLLC

(57) ABSTRACT

The invention relates to a kit for detecting biofilms, which is in particular compatible with the agri-food industry and comprises a biofilm staining solution containing a stain in solution in a dilution phase compatible with the agri-food industry, wherein said stain is Coomassie blue, and a cleaning solution comprising said dilution phase.

11 Claims, 2 Drawing Sheets

KIT FOR DETECTING BIOFILMS

This is a Divisional application of patent application Ser. No. 14/126,320, "KIT FOR DETECTING BIOFILMS" filed Dec. 12, 2013, which is a US National Stage application of International Application PCT/EP2012/062086 filed Jun. 22, 2012, which claims benefit of EP11171360.8 filed Jun. 24, 2011.

The present invention relates to a kit for detecting biofilms, in particular compatible with the agri-food industry.

Hygiene is of growing importance in the food industry, hospitals, water potabilization and desalination, process water treatment, and in particular in the water used in cooling towers and for daily use, for example for contact lenses. It is often noticed that, during the circulation of water or nutrient-rich substances on a substrate, microorganisms circulating freely in the water or in the nutritional material may adhere to the surface. These microorganisms may then develop an adhesive extracellular matrix made up of polymer substances.

A community of microorganisms adhered to the surface and encompassed in such a matrix is called a biofilm. Generally, these biofilms are made up of bacteria and organic polymers produced by the latter. Today, biofilms develop on all types of substrates, such as food conveyor belts in the agri-food industry, substrates intended to hold a nutritional substance, or in any case an organic substance, for any step whatsoever, for example meat hooks and similar mechanisms. Biofilms also develop on work surfaces in the hotel and catering industry, cleaning installations such as gutters, taps, sideboards, dishwashers, etc.

The presence of biofilms has also been observed in medical installations such as operating rooms and other medical devices where liquid phases are present (bodily fluids, aqueous cleaning phase after use, etc.).

Lastly, other industries are subject to the presence of biofilms, such as the paper industry, sewage treatment industry, and any other industry in which solid plant or organic materials are left to digest in the presence of water or a similar aqueous solution.

It has unfortunately been observed that this matrix is very resistant, and may constitute a barrier to agents that would act against microorganisms. The traditional sodium hydroxide-based treatments and/or treatments including different biocides are not effective enough, since they do not penetrate the entire thickness of the biofilm or are inhibited by certain molecules making up the matrix. The treatment is only partially effective on the upper surface of the biofilm. Furthermore, the latter may also trap microorganisms, in particular pathogens, other than that which initially became present. Simple cleaning of the installations is then generally not sufficient, and more specific treatment of the biofilm-contaminated areas is required.

Unfortunately, the specific biofilm treatments are more restrictive than a simple conventional cleaning step, and therefore require that the contaminated areas be easily identified. Although in certain cases, the extracellular matrix is easily identified when it is highly developed, in other cases, the biofilm develops insidiously in the installations and its presence is only detected during the quality analysis of the final product.

In the food industry field, biofilm formation is inevitable (in light of the richness of the surrounding environment). Biofilms have a cyclic growth activity comprising a growth phase, during which the accumulation of the microorganisms occurs, and a detachment phase, during which entire pieces of biofilms detach by erosion and under the effect of their own weight. When an industrialist is faced with this phenomenon, it is necessary in reality to stop the production chain and perform the cleaning cycle to eliminate the biofilm. However, this represents many hours of work and a loss of output of the installation. Furthermore, this type of detection makes it possible to determine that a biofilm is present somewhere, but does not make it possible to locate it precisely.

Consequently, in practice, production is not stopped and when the biofilm is in the rupture phase, product lots are contaminated and discarded until the microorganism contamination level of the food products is once again acceptable in light of the standards in force.

There is a therefore a need to be able to locate the presence of biofilms in this particularly restrictive type of installation precisely, since the manufactured products are intended to be ingested by living beings, but also in any type of industry subject to the possibility of biofilm development and for which that development represents an issue (e.g.: water treatment, cooling circuit, health, animal food, etc.), so as to be able to resolve it, periodically at any time, or for example between each production lot or each time production is stopped. In fact, if the surfaces of production devices have been sanitized correctly and are free of biofilms at the beginning of production, biofilm development will clearly be slower. However, if an invisible biofilm residue remains in the installations cleaned before production, that residue serves as a primer for biofilm development during the food production phase, which will inevitably lead to the waste of part of the production, contaminated by said biofilm.

Biofilm detection techniques have therefore been developed in recent years.

For example, document JP 2004/0023728 discloses a stain composition for detecting biofilms in the food industry containing red rice (Monascus red), which is vaporized on surfaces likely to contain biofilms.

This composition comprises 92% water, 4% stain and 4% ethanol. Although it is compatible with the food industry, this composition requires a high stain content, is not very compatible with an alkaline medium (traditionally used to sanitize installations), and has a color that is difficult to see (in all likelihood justifying the high content level of the stain).

Furthermore, as can be seen upon reading the comparative examples of the present patent application, some food substances are detected by Monascus red even though no biofilm is present.

The detection of false positives is truly problematic. It is in fact neither profitable nor ecological to begin treatments for surfaces believed to be contaminated by biofilms using specific substances when in reality there is no biofilm and there are simply food residues. It must in fact be understood that for industrialists, a step for eliminating biofilms generally requires stopping production installations, which represents a non-negligible cost and therefore must not be done unless necessary.

Document EP 1,491,505 discloses a method for measuring biofilm formation in aqueous systems. This method comprises a first step for placing test specimens in the aqueous system. It is then necessary to wait for a biofilm to develop before recovering the specimens. The specimens are next stained using a stain, rinsed, and analyzed by photometry or by comparison with a calibration card.

It is already possible to see that the detection method according to that invention has several drawbacks, in particular the fact that it reveals some uncertainties and that it is very long. In fact, specimens must be placed in areas where the presence of biofilms is suspected (leaving one to assume that they have already been previously detected), and it is necessary to wait for the development thereof. Although bacteria develop quickly, it cannot be ruled out that a biofilm may not develop on the specimen while the installation is covered with biofilms, or that the time during which the specimens are placed in the installation is not adequate for a biofilm to develop on the specimen, the bacteria still having a higher affinity for the extracellular matrix already formed on the installation to be treated than for the smooth surface of the test specimen.

Furthermore, according to the teaching of this document, before staining, the specimens are rinsed with azide to eliminate bacterial growth. The staining solution may be an aqueous solution of safranin, Coomassie blue, crystal violet, ruthenium red or erythionine. The rinse solution is a solution containing azide, and the specimens are lastly washed in DMSO after drying.

As can easily be seen, this described method cannot be applied in food methods, the azide $NaN_3$ is toxic and explosive, and it is dangerous to handle. As a result, in practice, this method is difficult to apply in any type of industry. In addition, DMSO is also not usable in the food industry. Lastly, the use of specimens is required, which limits this method to closed-circuit applications (the specimens must be placed for a period of up to five months).

This document further does not disclose any detection kit, uses bulky devices, and all of the examples use safranin and azide. No application of the teaching of this document is possible in the agri-food industry, and the color red is not adequate. In addition, the specimens are not applicable to open surfaces (conveyor belts) due to the high residence time (up to 5 months), the specimens being necessary in light of the toxicity of the substances used.

There is therefore a need to obtain a reliable, quick and compact detection kit, not requiring hard-to-use or hard-to-transport measuring apparatuses such as spectrometers, and the detection of which can be applied in any type of industry, for example such as the food industry.

The invention aims to offset the drawbacks of the state of the art by obtaining a kit for detecting biofilms making it possible to detect the presence of biofilms on any type of surface, that is particularly versatile, i.e., usable for any type of application, including in the agri-food industry, where from a sanitary perspective, the biofilms must be detected quickly, precisely and effectively, i.e., where the detection of false negatives and false positives is limited or even nonexistent.

To resolve this problem, according to the invention, a kit for detecting biofilms is provided as indicated at the beginning comprising a biofilm staining solution containing a stain in solution in a dilution phase compatible with the agri-food industry, wherein said stain is Coomassie blue, and a cleaning solution comprising said dilution phase.

As can be seen, the dilution phase of the stain is compatible with any type of application, but also with the agri-food industry, which makes it possible to apply it in any type of industrial installation, and the stain used is easily available on the market and particularly visible. Furthermore, the combination of the staining solution according to the invention and the cleaning solution makes it possible to reduce the detection of false positives and improves the selectivity of the detection relative to the existing detections.

In fact, according to the present invention, it is not bacteria detection that is desired, since that type of detection would inevitably provide false-negative results. In fact, when bacteria cause a biofilm to form, they develop an adhesive extracellular matrix made of polymer substances. The bacteria then adhere to the surface and are confined in the polymer matrix primarily made up of glycoproteins. It is therefore these glycoproteins that should be detected, and not the polysaccharides generally used in the prior art to detect the biofilms. Polysaccharide detection may provide a quantity of nonspecific results through the presence of false positives (polysaccharides are very present in residues in the agri-food industry) or false negatives. If the surface is well-cleaned and therefore few polysaccharides resulting from food residues are present, bacteria polysaccharides may not be detected, given that the bacteria are confined in that polymer matrix and are therefore not accessible for staining, especially if the waiting time of the stain is not long.

Additionally, generally, red-based stains are used. However, they are not very visible, if they manage to reach the polysaccharides of the bacteria confined in the biofilms, through that matrix making up the biofilm.

That is why the kit according to the invention has a speed of detection and specificity that are very advantageous, since it targets the glycoproteins of the extracellular matrix of the biofilm and therefore reduces the presence of false negatives or false positives and targets the glycoproteins that are very accessible by the stain and not very present in foods or other residues. The biofilm is therefore detected quickly and selectively.

The detection kit according to the invention simply comprises a first solution to be vaporized and a second cleaning solution to be vaporized next, the wait times of which are short (less than 15 minutes). This means that generally, in less than one hour, preferably in less than a half-hour, the biofilms are detected and precisely located.

The practical aspect of the kit according to the invention is particularly advantageous in that it does not require a costly installation to detect the biofilm; the user's eye suffices, owing to the particular choice of the stain, which is easily identifiable to the naked eye, different from the colors generally found in all types of industries processing plant or organic materials (small number of blue foods, as opposed to red). A simple vaporization of the first solution, then the second is sufficient.

Advantageously, the detection kit according to the invention further comprises a bleaching composition, compatible with the agri-food industry, which next makes it possible to cause the blue color to disappear from the installation if necessary. In fact, in certain applications, the materials used are porous, such as the rubbers of conveyor belts. So as not to keep the blue color on those specific materials, a bleaching solution will be used. It is in fact not advantageous for the blue color to remain after use, since that could harm the subsequent detection steps. The blue color of the biofilm is of course eliminated with the biofilm.

In one particular embodiment, said bleaching composition is a solid phase of an oxidizing agent that may simply be spread over the treated area, preferably previously wetted to favor the activation of the oxidizing agent in the water. The presence of the bleaching composition in the form of a solid phase is advantageous for preserving the oxidizing nature of the bleaching composition over time.

In one alternative according to the invention, said bleaching composition is an aqueous solution of an oxidizing agent, which allows it to be applied easily on the area to be treated by simple vaporization, especially when it is vertical.

In one particular embodiment of the biofilm detecting kit according to the invention, said oxidizing agent is chosen from the group consisting of sodium percarbonate, sodium hypochlorite, hydrogen peroxide, perborates, persulfates, or peroxides, or mixtures and derivatives thereof, for example such as urea percarbamate.

In particular, said dilution phase comprises from 35 to 55%, preferably from 40 to 50%, still more preferably approximately 45% by volume of ethanol, in particular absolute ethanol, relative to the final volume of said dilution phase, from 7 to 13%, preferably from 8 to 12%, more particularly approximately 10% by volume of acetic acid, in particular glacial acetic acid, relative to the final volume of said dilution phase, and from 35 to 55%, preferably from 40 to 50%, more preferably approximately 45% by volume of water, relative to the final volume of said dilution phase.

As one can easily see, this dilution phase only comprises ingestible substances compatible with the agri-food industry, but is not strictly limited thereto, that are easy to obtain and inexpensive.

Other embodiments of the detection kit according to the invention are indicated in the appended claims.

The invention also relates to a method for detecting biofilms, in particular using the kit according to the present invention.

This method is characterized in that it comprises the following steps:
vaporizing a biofilm staining solution containing a stain in solution in a dilution phase compatible with the agri-food industry, in which said stain is Coomassie blue, on a surface that may be contaminated by a biofilm,
staining said biofilm for a predetermined period of time with said staining solution,
vaporizing a cleaning solution,
diluting said excess staining solution using the cleaning solution during a predetermined period of time, and
detecting said biofilm by observing residual areas colored with Coomassie blue corresponding to biofilms colored by said stain.

As previously mentioned, the method according to the present invention is quick, inexpensive in terms of time and the equipment to be used, effective through its selectivity and detection speed, and compatible with the agri-food industry, therefore versatile for any type of industry.

Advantageously, one or more of the steps chosen from the group consisting of the step for vaporizing said staining solution, vaporizing said cleaning solution, and detecting said biofilm is preceded by a step for rinsing with water, which makes it possible to eliminate the excess stain, on the area to be treated or diluted in the cleaning solution, which makes it possible to improve the selectivity of the biofilm detecting method according to the invention.

In one preferred embodiment according to the present invention, the method further comprises a step for bleaching said residual areas stained with Coomassie blue by applying a bleaching composition.

Advantageously, said bleaching step is carried out by applying a solid bleaching composition, in particular powdered, of an oxidizing agent, on the surface to be treated, previously wetted to favor activation of the oxidizing agent.

In one alternative according to the invention, said bleaching step is carried out by applying a liquid bleaching composition of an oxidizing agent.

Preferably, according to the invention, said predetermined period of time is comprised between 3 and 15 minutes, preferably between 4 and 10 minutes, and is generally approximately 5 minutes. This of course makes it possible to detect the biofilm quickly, but also reflects the effectiveness of the method according to the invention, which may be implemented quickly, and its selectivity (the substance to be detected is truly targeted and quickly detected).

Still more preferably, said surface that may be contaminated by a biofilm is an open surface of an installation, in particular an installation in the agri-food industry. It is in fact preferable for the surface on which the biofilm must be detected by the method according to the invention to be a surface visible to the naked eye, which is generally called an open surface. However, the method according to the invention may also be applied on less accessible surfaces or surfaces that are not visible, but they will of course need to be disassembled for the detection step; for example, tubings may be treated, for example by circulation, but they must in all likelihood be opened to detect the result.

Of course, although it is not necessary according to the present invention, the method may also use specimens placed in closed installations. Once recovered, the specimens are then treated like any other open surface within the meaning of the present invention.

Other embodiments of the inventive method are indicated in the appended claims.

The present invention also relates to a use of a solution for staining biofilms containing a stain in solution in a dilution phase compatible with the agri-food industry, in which said stain is Coomassie blue, on a surface that may be contaminated by a biofilm, preferably on an open surface, in particular in an installation in the agri-food industry.

Other embodiments of the use according to the invention are indicated in the appended claims.

Other features, details and advantages of the invention will emerge from the description thereof provided below, non-limitingly and in reference to the aforementioned examples.

In the figures, identical or similar elements bear the same references.

Figure 1:
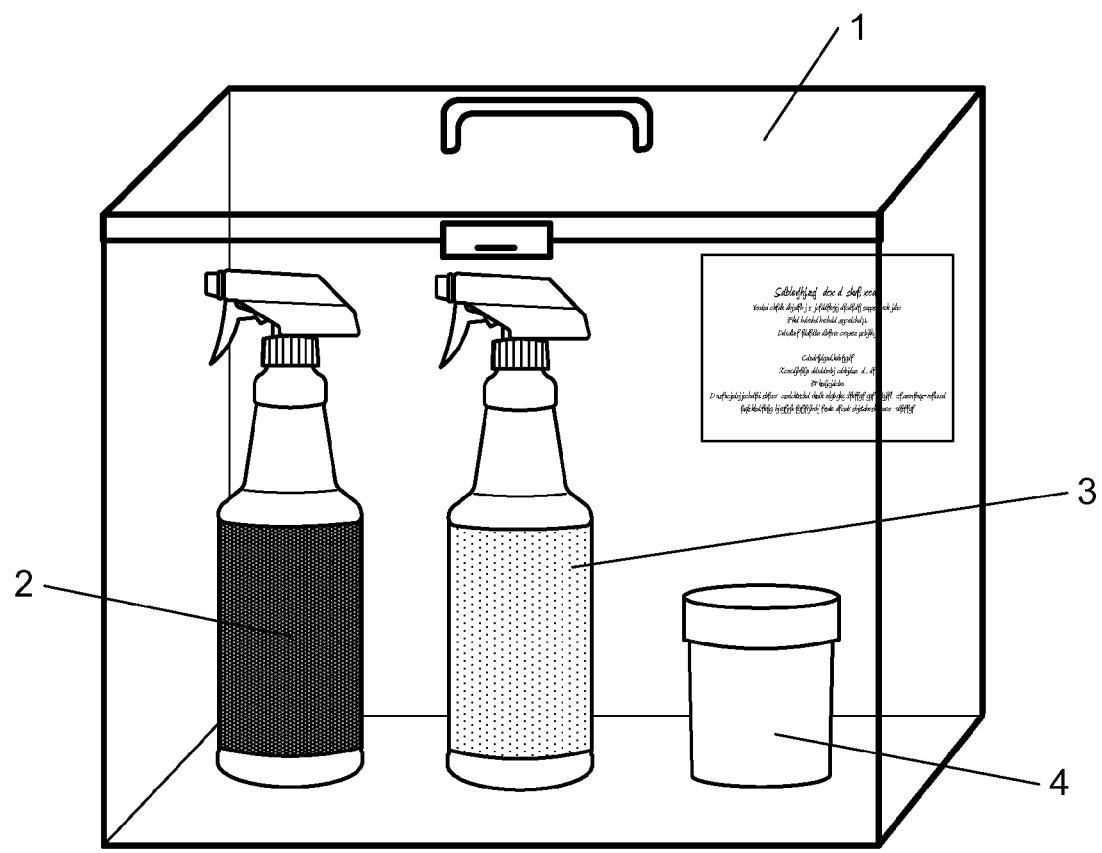
FIG. 1 is a perspective view of a kit for detecting biofilms according to the invention.

FIG. 1 illustrates the kit 1 for detecting biofilms comprising a staining solution 2 for staining biofilms containing Coomassie blue in solution in a dilution phase compatible with the agri-food industry. The stain may of course, depending on the required applications, optionally comprise another stain in a mixture, but will in any case include Coomassie blue with the aim of detecting the biofilms.

The phase for diluting the staining solution 2 comprises, in this illustrated advantageous embodiment, 45% by volume of absolute ethanol, 10% by volume of glacial acetic acid, and 45% by volume of water relative to the final volume of the dilution phase.

The detection kit 1 further comprises a cleaning solution 3 advantageously made up of said dilution phase. This of course makes it possible to dilute the stain not bonded to the proteins of the biofilm.

The kit 1 for detecting biofilms advantageously further comprises a bleaching composition 4, compatible with the agri-food industry. In the illustrated embodiment, the bleaching composition 4 is a solid phase of an oxidizing agent made up of sodium percarbonate. In one alternative (not illustrated) according to the invention, the bleaching composition 4 is an aqueous solution of an oxidizing agent, for example such as a sodium hypochlorite or hydrogen peroxide solution.

In one advantageous use of the kit 1 for detecting biofilms, first, the surface to be treated to detect whether a biofilm is present, for example an open surface in the agri-food industry, is rinsed and then vaporized with the staining solution 2. The stain is allowed to act for approximately 5 minutes, and the surface to be treated is next rinsed to eliminate the excess staining solution therefrom. Generally, the quantity of staining solution used will be approximately 6.5 µl/cm$^2$ of surface to be treated, i.e., 65.2 ml/m$^2$.

The surface to be treated is next, according to recommendations, vaporized using the cleaning solution 3, which is left to work for approximately 5 minutes. The cleaning solution is advantageously made up of the dilution phase of the stain of the staining solution 2 of the kit for detecting biofilms according to the present invention. The cleaning solution therefore makes it possible to eliminate any traces of excess Coomassie blue that does not adhere to the biofilm by dilution effect in the dilution phase. Generally, the quantity of staining solution used will be approximately 21.7 µl/cm$^2$ of surface to be treated, i.e., 217 ml/m$^2$.

The surface is next rinsed with water to eliminate traces of residual Coomassie blue diluted in the cleaning solution 3, and the surface to be treated is then left to rest for 5 minutes. When the blue stain remains on the surface to be treated, it indicates the presence of a biofilm and therefore allows it to be detected quickly in approximately less than 20 minutes. Lastly, the bleaching composition in the form of a powdered reagent in the kit according to the invention is distributed over the wet surface to be treated to eliminate the blue stain from the surface to be treated.

EXAMPLE 1

Five sets of different specimens were recovered from different organic materials frequently used in the agri-food industry according to the protocols stated below.
a) butter: the specimens were manually coated with butter
b) starch: specimens are placed in a bowl and cover with one ml of rice cooking water, rich in starch. The specimens are next left to dry in the open air.
c) carboxymethylcellulose: specimens are placed in a bowl and covered with one ml of a carboxymethylcellulose (CMC) solution. The specimens are next left to dry in the open air. The concentration of carboxymethylcellulose of the solution used is 500 mg of CMC/50 mL of demineralized water.
d) gelatin: specimens are placed in a bowl and covered with one ml of a gelatin solution. The specimens are then left to dry in the open air. The concentration of the gelatin solution is 3.6% gelatin, obtained by dissolving 3.6 g of commercial gelatin in 100 ml of hot water.
e) milk: specimens are placed in a bowl and 1 ml of a solution of milk diluted 100 times by water is poured on each specimen. The specimens are then left to dry in the open air.

The specimens are then placed for 30 minutes in the stain solution containing approximately 0.25 g of Coomassie blue R250 in a dilution phase comprising 45 ml of pure ethanol, 45 ml of distilled water and 10 ml of glacial acetic acid. The specimens are next submerged in 100 ml of cleaning solution made up of approximately the same dilution phase. Next, the specimens were left to dry in the open air.

A visual analysis of the specimens makes it possible to see that the butter, carboxymethylcellulose, gelatin and starch are not stained by the Coomassie blue. Slight traces remain with the milk diluted 100 times.

As one can see, the kit for detecting biofilms according to the present invention makes it possible to detect the biofilms with great specificity.

EXAMPLE 2

Industrial Example in an Agri-Food Industry

Installations of a slaughterhouse were, after conventional cleaning, tested for the presence of biofilms using the kit according to the invention. The installations after conventional cleaning have a very good visual appearance of cleanliness. The areas tested for biofilm detection are primarily the plucking, evisceration and trussing rooms.

On the slightly wet surfaces, the staining solution of the kit according to the invention was vaporized on all of the devices of those rooms such as hooks, hard head, blades, stainless steel containers, buckets, etc. and left to work for 5 minutes. The staining solution comprising 0.1 g of Coomassie blue in 100 ml of dilution phase comprising 45 ml of water, 45 ml of absolute ethanol and 10 ml of glacial acetic acid.

Figure 2:
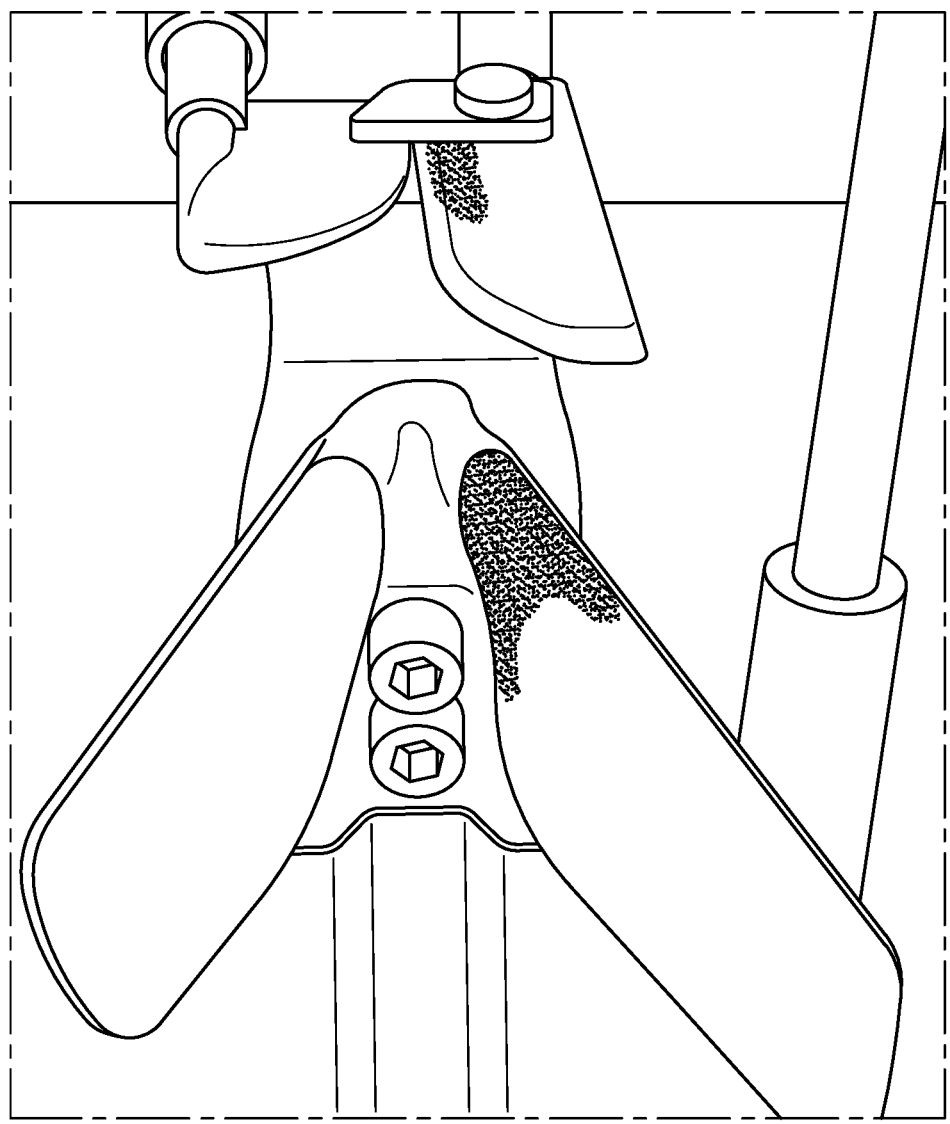
FIG. 2 is a photograph of an element in the agri-food industry treated using the kit for detecting biofilms according to the present invention, showing the detection of biofilms.

The surfaces of the tested elements were rinsed with water to eliminate the excess stain, then vaporized with the cleaning solution comprising said dilution phase. The cleaning solution was left to work for 5 minutes, and the elements tested for biofilm detection were rinsed and mechanically rubbed to provide a slight mechanical action and eliminate the residual stains and/or any false positives. The results were then observed. It is very easy to see that the problems of remanent contamination on certain surfaces are caused by the presence of biofilms, as for example on the test elements such as plucking hooks, blades, buckets, containers and head hooks. Only the head hooks are illustrated in FIG. 2, while the other elements are also contaminated. Despite the quality of the cleaning done by the company, certain apparatuses are contaminated, sometimes seriously contaminated, by a biofilm. This biofilm is the source of noncompliant microbiological results.

COMPARATIVE EXAMPLE 1

The 5 sets of different specimens of example 1 according to the invention were covered by the same different organic materials frequently used in the agri-food industry, with the exception of the fact that for milk, two tests were done, in which the dilution of the milk applied was 100 times as in example 1, as well as 20 times.

The specimens are then placed in the stain solution containing approximately 3 g of red rice (Monascus red) in 100 ml of a dilution phase comprising water and ethanol in a 1/1 ratio for 15 minutes, then for rinsing, 10 minutes in distilled water.

A visual analysis of the specimens makes it possible to see that the butter and carboxymethylcellulose are not stained by the red rice (Monascus red), whereas the milk (at both dilutions), starch and gelatin are stained by that stain, which makes it non-specific and complex to use. It must be noted here that the test protocol according to prior document JP 2004/0023728 was adapted to be able to compare the results with those obtained for the kit according to the present invention.

COMPARATIVE EXAMPLE 2

The 5 sets of different specimens from example 1 according to the invention were covered with the same different organic materials frequently used in the agri-food industry, with the exception of the fact that for milk, two tests were done, in which the applied dilution of the milk was 100 times as in example 1, as well as 20 times.

The specimens are then positioned in the stained solution containing approximately 36 g/l of safranin in a dilution phase comprising demineralized water, methyl ethyl ketone and ethanol for 15 minutes, then for rinsing, 10 minutes in demineralized water.

A visual analysis of the specimens makes it possible to see that the butter, carboxymethylcellulose and gelatin are not stained by the safranin, whereas the milk (at both dilutions) and the starch are stained by that stain, which makes it non-specific and complex to use. It must be noted here that the test protocol according to prior document EP 1,491,505 was suitable on the one hand to be applicable in the agri-food industry, and on the other hand to be able to compare the results with those obtained for the kit according to the present invention.

It is of course understood that the present invention is in no way limited to the embodiments described above and that modifications may be made thereto without going beyond the scope of the appended claims.

The invention claimed is:

1. A method for detecting a biofilm on an installation comprising the following steps:
   (a) contacting an open surface of an installation that may be contaminated by a biofilm with a biofilm staining solution for a predetermined period of time of less than 15 minutes, wherein the staining solution consists of Coomassie blue in solution in a dilution phase compatible with the agri-food industry, and wherein said surface is initially contacted by spraying said biofilm staining solution on the open surface,
   (b) contacting said open surface of the installation with a cleaning solution comprising said dilution phase for a predetermined period of time of less than 15 minutes thereby diluting excess stain not bonded to the biofilm, wherein said open surface is initially contacted with the cleaning solution by spraying said cleaning solution on the open surface, and
   (c) detecting a presence and a precise location of biofilm on the installation by visually observing residual areas colored with Coomassie blue corresponding to the biofilm colored by said stain on the installation, wherein said method for detecting the biofilm is performed in less than one hour.

2. The method according to claim 1, wherein one or more of steps a, b, and c is preceded by a step for rinsing said surface with water.

3. The method according to claim 1, further comprising a step for bleaching residual areas stained with Coomassie blue by applying a bleaching composition.

4. The method according to claim 3, wherein said bleaching step is carried out by applying a solid powdered bleaching composition of an oxidizing agent, on the surface to be treated, previously wetted to favor activation of the oxidizing agent.

5. The method according to claim 3, wherein said bleaching step is carried out by applying a liquid bleaching composition of an oxidizing agent.

6. The method according to claim 1, wherein said predetermined period of time for contacting said staining solution with said staining solution is between 4 and 10 minutes.

7. The method according to claim 1, wherein said open surface that may be contaminated by a biofilm is a surface of an installation in the agri-food industry, water treatment, cooling circuit and animal food industry.

8. The method according to claim 1, wherein said dilution phase comprises from 35 to 55% by volume of ethanol, relative to the final volume of said dilution phase, from 7 to 13% by volume of acetic acid, relative to the final volume of said dilution phase, and from 35 to 55% by volume of water, relative to the final volume of said dilution phase.

9. The method according to claim 4 wherein said oxidizing agent is chosen from the group consisting of sodium percarbonate, sodium hypochlorite, hydrogen peroxide, perborates, persulfates, peroxides, mixtures thereof, and derivatives thereof.

10. The method according to claim 5 wherein said oxidizing agent is chosen from the group consisting of sodium percarbonate, sodium hypochlorite, hydrogen peroxide, perborates, persulfates, peroxides, mixtures thereof, and derivatives thereof.

11. The method according to claim 6, wherein said predetermined period of time for contacting said open surface with said cleaning solution is between 4 and 10 minutes.

* * * * *